US008088725B2

(12) United States Patent
Dang et al.

(10) Patent No.: US 8,088,725 B2

(45) Date of Patent: Jan. 3, 2012

(54) FRAGRANCE COMPOSITIONS AND COMPOUNDS

(75) Inventors: Hai-Shan Dang, Shanghai (CN); Simon Ellwood, Ashford (GB); Anne-Dominique Fortineau, Asnières sur Seine (FR); Christopher Furniss, Uster (CH)

(73) Assignee: Givaudan Nederland Services B.V., Naarden (NL)

( * ) Notice: Subject to any disclaimer, the term of this patent is extended or adjusted under 35 U.S.C. 154(b) by 115 days.

(21) Appl. No.: 12/524,513

(22) PCT Filed: Jan. 31, 2008

(86) PCT No.: PCT/EP2008/000752

§ 371 (c)(1), (2), (4) Date: Jul. 24, 2009

(87) PCT Pub. No.: WO2008/092678

PCT Pub. Date: Aug. 7, 2008

(65) Prior Publication Data

US 2010/0132249 A1 Jun. 3, 2010

(30) Foreign Application Priority Data

Feb. 2, 2007 (GB) .................................. 0702017.5

(51) Int. Cl.
*A61K 8/18* (2006.01)

(52) U.S. Cl. .............. 512/27; 512/25; 512/26; 568/420; 568/448

(58) Field of Classification Search .................... 512/25, 512/26, 27; 568/420, 448

See application file for complete search history.

(56) References Cited

U.S. PATENT DOCUMENTS

| | | | |
|---|---|---|---|
| 4,324,921 | A | 4/1982 | Arpe |
| 4,709,097 | A | 11/1987 | Hoelderich et al. |
| 5,012,005 | A | 4/1991 | Hoelderich et al. |

FOREIGN PATENT DOCUMENTS

| | | | |
|---|---|---|---|
| FR | 0673379 | A | 6/1930 |
| JP | 61-134337 | * | 6/1986 |
| JP | 61134337 | A | 6/1986 |
| WO | WO 01/04078 | A1 | 1/2001 |

OTHER PUBLICATIONS

Arndt, Henry C., et al., *Synthesis of a-Alkoxy-, a-Aryloxy-, and z-Benzyloxyacetaldehydes*, Synthesis. 1979, vol. 3, pp. 202-204.

Gaiffe. Andre, et al., *Obtention de cyanoéthers per action de l'acrylonitrile sur les alcools terpéniques en présence de triton B. Obtention d'aldoéthers par réduction catalytique des cyanoéthers correspondants en présence de semicarbazide*, Comptes Rendus des Secances de l'Academie des Sciences. 1969, pp. 989-991, vol. 269(17).

Kulka, Kurt, et al., *Novel Oxy-acetaldehydes and Some of Their Derivatives In Perfumery*, American Perfumer and Cosmetics, Jun. 1967, vol. 82, pp. 29-30.

Mandai, Tadakatsu, et al., *Novel Synthesis and Applications of Mixed Acetals (Acetyl Methyl Acetals)*, Terahedron Letters, 1984, vol. 25, No. 22, pp. 2371-2374, Pergamon Press, Ltd., Great Britain.

Masaki, Yukio, et al, *Substrate-Specific Rearrangement and Acetonidation of Epoxy-Ethers Catalyzed by Tetracyanoethylene*, Chemistry Letters, 1993, pp. 17-20.

Rothbart, Marcu, *Sur quelque nouveaux acétals et aldéhydes à fonction éther-oxyde*, Comptes Rendus des Secances de l'Acadamie des Sciences, 1993, pp. 2013-2015, vol. 196, France.

PCT/EP2008/000752—Written Opinion of the International Searching Authority, Jul. 29, 2009.

PCT/EP2008/000752—International Search Report, Jul. 29, 2009.

GB 0702017.2—Great Britain Search Report, May 4, 2007.

* cited by examiner

*Primary Examiner* — Cephia D Toomer
*Assistant Examiner* — Monique Cole
(74) *Attorney, Agent, or Firm* — Curatolo Sidoti Co., LPA; Joseph G. Curatolo; Salvatore A. Sidoti

(57) ABSTRACT

A perfume composition including the compound 4-[(1,5-dimethylhexyl)oxy]butanal in both its racemic and enantiomeric forms.

9 Claims, No Drawings

FRAGRANCE COMPOSITIONS AND COMPOUNDS

CROSS REFERENCE TO RELATED APPLICATIONS

This application is a national stage application of International Application No. PCT/EP2008/000752, filed 31 Jan. 2008, which claims the benefit of Great Britain Patent Application Serial No. 0702017.5, filed 2 Feb. 2007, from which applications priority is claimed and which are incorporated herein by reference.

FIELD OF THE INVENTION

The invention relates to the discovery of novel fragrance compounds, and perfumes and perfumed products comprising the novel compounds.

BACKGROUND

A major area of interest in the fragrance industry is to find high odour impact fragrance materials which can provide superior performance at lower concentrations giving cost savings and lower environmental impact.

Muguet (Lily of the Valley) is an important area in perfumery (M Boelens and H Wobben, Perfumer & Flavorist, 1980, 5 (6), 1-8) and the odour is created by a combination of fragrance ingredients, each providing a different facet to the complex odour character. There are a number of aldehydic materials that possess alicyclic terpenoid-like structures are non-aromatic and possess odour characters valuable for muguet accords eg Trimenal™, Adoxal™ and Profarnesal™.

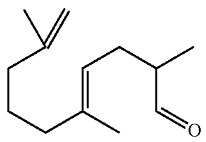

Trimenal

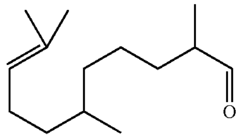

Adoxal

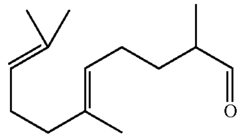

Profarnesal

Structurally based on such materials, citronellyl oxy-acetaldehyde (1) is a valuable ingredient which is described as possessing a powerful, moderately diffusive, green, rosy, sweet Lily-Muguet-like odour (S. Arctander, Perfume And Flavor Chemicals, 1969).

(1)

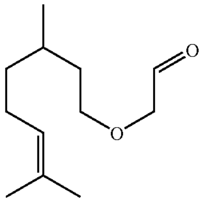

SUMMARY OF THE INVENTION

It has now been found that certain compounds provide a high odour impact covering a range of odour characteristics valuable to floral/muguet perfume accords. There is therefore provided a perfume composition, comprising at least one compound of Formula I

I

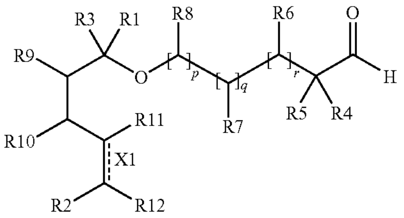

wherein p, q and r are independently selected from 0 and 1, p+q+r being from 0-3 and X1 is saturated or unsaturated, such that:

(a) when p+q+r=0, R1, R2 and R12 are Me; R3-5 and R9-11 are H;

(b) when p+q+r=1, R1 and R12 are independently selected from H, Me and Et; R2 is selected from H and $C_1$-$C_4$ alkyl; R3-5 and R9 are independently selected from H and methyl; and R8 and R10 are H;

(c) when p+q+r=2, R1 and R2 are selected from H and $C_1$-$C_4$ alkyl, R3 and R9-12 are independently selected from H and methyl; R4-5 are H, or R4 and R5 together form a methylene group; and R6-7 are H;

(d) when p+q+r=3, R1, R2 and R12 are Me; and R3-11 are H.

These compounds have been surprisingly found to have a strong and pleasant odour and are suitable for use as perfume ingredients, particularly in Muguet accords/fragrances.

Particular embodiments are those in which, independently:

X1 is saturated;

at least one of R1, R4, R5, R9, R10 is H;

at least one of R3, R12 is methyl;

R2 is $C_1$ to $C_4$ alkyl, preferably methyl.

In a further embodiment, p+q+r=2.

Some of the compounds according to Formula I are novel. Therefore, there is also provided a compound of Formula I, as shown hereinabove, wherein p, q and r are independently selected from 0 and 1, p+q+r being from 0-3 and X1 is saturated or unsaturated, such that:

(a) when p+q+r=0, R1, R2 and R12 are Me; R3-5 and R9-11 are H;

(b) when p+q+r=1, R1 and R12 are independently selected from H, Me and Et; R2 is selected from H and $C_{1-4}$ alkyl; R3-5 and R9 are independently selected from H and methyl; and R8 and R10 are H;

(c) when p+q+r=2, R1 is selected from H and $C_1$-$C_4$ alkyl; R2 is selected from H, methyl, propyl and butyl; R3 and R9-12 are independently selected from H and methyl; R4-5 are H, or R4 and R5 together form a methylene group; and R6-7 are H; (d) when p+q+r=3, R1, R2 and R12 are Me; and R3-11 are H.

Particular embodiments are those in which, independently:

X1 is saturated;

at least one of R1, R4, R5, R9, R10 is H;

at least one of R3, R12 is methyl;

R2 is methyl.

In a further embodiment, p+q+r=2.

In a further aspect, there is provided a perfumed product comprising a novel fragrance compound or perfume composition, as hereinabove described.

There is also provided a method of providing a perfumed product with a muguet-like fragrance accord, comprising adding to a product base a perfume composition or a compound as hereinabove described.

Some specific examples of compounds according to this disclosure are presented below.

| Material | Odour Character |
|---|---|
| 4-[(5-methylhexyl)oxy]butanal | Aldehydic, Fatty, caramel |
| 4-[(4-methylpentyl)oxy]butanal | Aldehydic, Green |
| 2-methyl-3-[(5-methylhexyl)oxy]propanal | Aldehydic, Citrus, Lemon, Nerol Like |
| 2-methyl-3-[(4-methylpentyl)oxy]propanal | Aldehydic, Green, Watery, Nitrile |
| 5-[(1,5-dimethylhexyl)oxy]pentanal | Aldehydic, Marine, Floral |
| 4-[(1,5-dimethylhexyl)oxy]butanal | Aldehydic, green, floral, watery, very intensive and diffusive |
| 4-{[(1R)-1,5-dimethylhexyl]oxy}butanal | Aldehydic, floral, citrus, muguet, lower intensity than racemic |
| 4-{[(1S)-1,5-dimethylhexyl]oxy}butanal | Aldehydic, floral, green, watery, more intensive and diffusive than racemic |
| 4-[(1,5-dimethylheptyl)oxy]butanal | Aldehydic, caramel, fatty |
| 4-[(1,4,5-trimethylhexyl)oxy]butanal | Aldehydic, muguet, citrus, freshair |
| 4-[(1,5-dimethylhexyl)oxy]-2-methylbutanal | Aldehydic, mandarin |
| 2-{2-[(1,5-dimethylhexyl)oxy]ethyl}acrylaldehyde | Aldehydic, fatty, |
| 4-[(1-methylpentyl)oxy]butanal | Aldehydic, green, marine |
| 4-[(1,5,7-trimethyloctyl)oxy]butanal | Aldehydic, citrus, green, fatty |
| 3-[(1,5-dimethylhexyl)oxy]-2-methylpropanal | Aldehydic, floral, watery |
| 3-{[(1R)-1,5-dimethylhexyl]oxy}-2-methylpropanal | Aldehydic, citrus |
| 3-{[(1S)-1,5-dimethylhexyl]oxy}-2-methylpropanal | Aldehydic, citrus, marine |
| 3-[(1,5-dimethylhex-4-enyl)oxy]-2,2-dimethylpropanal | Aldehydic, fruity, floral, citrus |
| 4-{[(4Z)-1,1,5-trimethylhept-4-enyl]oxy}butanal | Aldehydic, green |
| 4-[(1,1,5-trimethylheptyl)oxy]butanal | Aldehydic, minty, linalol oxide-like |
| 4-[(1,1-dimethylpentyl)oxy]butanal | Aldehydic, camphoraceous, spicy, cucumber |
| 4-[(1-ethyl-1,5-dimethylhexyl)oxy]butanal | Aldehydic, floral, green, lemon |
| 4-[(1-ethyl-1,5-dimethylhex-4-enyl)oxy]butanal | Floral, aldehydic, muguet |
| 4-[(1,1,5,7-tetramethyloctyl)oxy]butanal | Floral, fatty, aldehydic, muguet |
| 4-[(1,1,4,5-tetramethylhexyl)oxy]butanal | Floral, fatty, fruity, ambergris |
| 4-[(1,1,4,5-tetramethylhex-4-enyl)oxy]butanal | Aldehydic, fruity |
| 4-[(1-ethyl-1,5-dimethylheptyl)oxy]butanal | Aldehydic, floral, muguet |
| 2-methyl-3-{[(4Z)-1,1,5-trimethylhept-4-enyl]oxy}propanal | Floral, aldehydic, metallic, fatty |
| 2-methyl-3-[(1,1,5-trimethylheptyl)oxy]propanal | Floral, aldehydic, muguet, marine, rose |
| 3-[(1,1-dimethylpentyl)oxy]-2-methylpropanal | Herbal, aldehydic, minty, camphoraceous, pine american |
| 3-[(1-ethyl-1,5-dimethylhexyl)oxy]-2-methylpropanal | Aldehydic, citrus, floral, orange |
| 3-[(1-ethyl-1,5-dimethylhex-4-enyl)oxy]-2-methylpropanal | Floral, watery, muguet, citrus, orange |
| 2-methyl-3-[(1,1,5,7-tetramethyloctyl)oxy]propanal | Aldehydic, fatty, cucumber, floral |
| 2-methyl-3-[(1,1,4,5-tetramethylhexyl)oxy]propanal | Floral, aldehydic |
| 2-methyl-3-[(1,1,4,5-tetramethylhex-4-enyl)oxy]propanal | Floral, aldehydic |
| 3-[(1-ethyl-1,5-dimethylheptyl)oxy]-2-methylpropanal | Aldehydic, floral, fruity |
| [(1,5-dimethylhexyl)oxy]acetaldehyde | Aldehydic, green, floral, very strong |
| 2,2-dimethyl-3-(pentyloxy)propanal | Fruity, -valerianic, green-herbaceous, bitter & earthy, nutty |
| 2-(2,5,7-trimethyloctyloxy)acetaldehyde | Aldehydic, metallic, fatty, intense, leafy (parsley leaf), citrus |

Particular specific embodiments are
4-[(1,5-dimethylhexyl)oxy]butanal;
4-[(1-methyl,5-ethylhexyl)oxy]butanal; and
4-[(1,4,5-trimethylhexyl)oxy]butanal.

These are high performing materials possessing aldehydic, green, caramel, watery and muguet odour character, 4-[(1,5-dimethylhexyl)oxy]butanal being particularly diffusive.

Surprisingly 4-[(1,1,5-trialkyl hexyl)oxy]butanals and in particular 3-[(1-ethyl-1,5-dimethylhex-4-enyl)oxy]-2-methyl-propanal possess significantly more floral/muguet character than butanals hitherto known to and used by the art.

The odour properties of the aldehydes of the invention mean that an aldehyde, (including corresponding acetals or Schiffs bases), or mixture of aldehydes in accordance with the invention, may be used as such to impart, strengthen or improve the odour of a wide variety of products, or may be used as a component of a perfume (or fragrance composition) to contribute its odour character to the overall odour of such perfume.

The compounds of Formula I are described herein without reference to stereochemistry. However, it will be clear that a number of the compounds have one or more chiral centres, and thus give rise to two or more enantiomers. It is well known in the art that certain enantiomers will have odours that are different in either or both of strength and character from that of other enantiomers. As it is also well known that there is no way of predicting the odour properties of individual enantioners, and the differences can range from no olfactory difference to considerable, surprising difference. Thus, either complete separation or enrichment of one or more enantiomers can sometimes be beneficial. Against this is the fact that such separation can add significantly to the cost of providing a molecule, so a cost-benefit balance may need to be struck for each molecule.

The effect that stereochemistry can have is shown by reference to the isomers and racemate of 4-[(1,5-dimethylhexyl) oxy]butanal:

| | |
|---|---|
| 4-[(1,5-dimethyl-hexyl)oxy]butanal (racemate) | Aldehydic, green, floral, watery, very intensive and diffusive |
| 4-{[(1R)-1,5-dimethyl-hexyl]oxy}butanal | Aldehydic, floral, citrus, muguet, lower intensity than racemate |
| 4-{[(1S)-1,5-dimethyl-hexyl]oxy}butanal | Aldehydic, floral, green, watery, more intensive and diffusive than racemate |

For the purposes of this disclosure, a perfume composition means a mixture of fragrance compounds, if desired mixed with or dissolved in a suitable solvent or mixed with a solid substrate.

The quantities in which one or more fragrance compounds according to the invention can be used in perfumes may vary within wide limits and depend, inter alia, on the nature and the quantity of the other components of the perfume in which the aldehyde is used and on the olfactive effect desired. It is therefore only possible to specify wide limits, which, however, provide sufficient information for the specialist in the art to be able to use an aldehyde according to the invention for his specific purpose. Typically, a perfume comprises one or more fragrance compounds in accordance with the invention in an olfactively effective amount. In perfumes an amount of 0.01% by weight or more of a fragrance compound according to the invention will generally have a clearly perceptible olfactive effect. Preferably the amount is from 0.1 to 80% by weight, more preferably at least 1% by weight.

A perfume composition as hereinabove described may be added to a product base to provide a perfumed product. By "product base" is meant the totality of ingredients required to make a product, apart from the perfume composition.

Example of perfumed products are: fabric washing powders, washing liquids, fabric softeners and other fabric care products; detergents and household cleaning, scouring and disinfection products; air fresheners, room sprays and pomanders; soaps, bath and shower gels, shampoos, hair conditioners and other personal cleansing products; cosmetics such as creams, ointments, toilet waters, pre-shave, aftershave, skin and other lotions, talcum powders, body deodorants and antiperspirants, etc.

The amount of the fragrance compound according to the invention present in products will generally be at least 10 ppm by weight, preferably at least 100 ppm, more preferably at least 1000 ppm. However, levels of up to about 20% by weight may be used in particular cases, depending on the product to be perfumed.

It has also been surprisingly discovered that certain fragrance compounds in accordance with the invention show good substantivity to hair and cloth, both wet and dry, and hence have good potential for use in fabric treatment products and hair care products.

Preparation

The compounds according to the invention may be prepared according to procedures known in the art. Compounds such as the 4-[(1,5-dialkylhexyl)oxy]butanals, 4-[(1,4,5-trialkylylhexyl)oxy]butanals, 4-[(1,3,5-trialkylhexyl)oxy]butanals, 4-[(1,2,5-trialkylhexyl)oxy]butanals and 5-[(1,5-dimethylhexyl)oxy]pentanal may be prepared via a range of possible synthetic routes a number of examples are shown in Scheme 1 (using 4-[(1,5-dimethylhexyl)oxy]butanal as a representative example).

Scheme 1

1

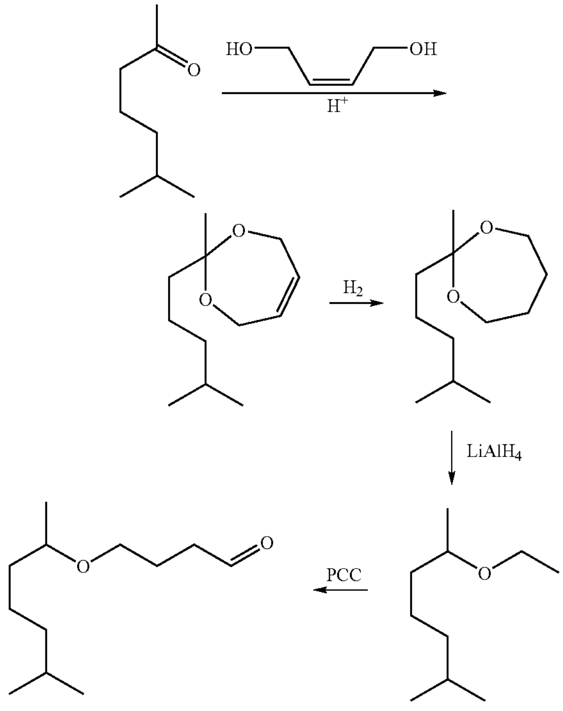

2

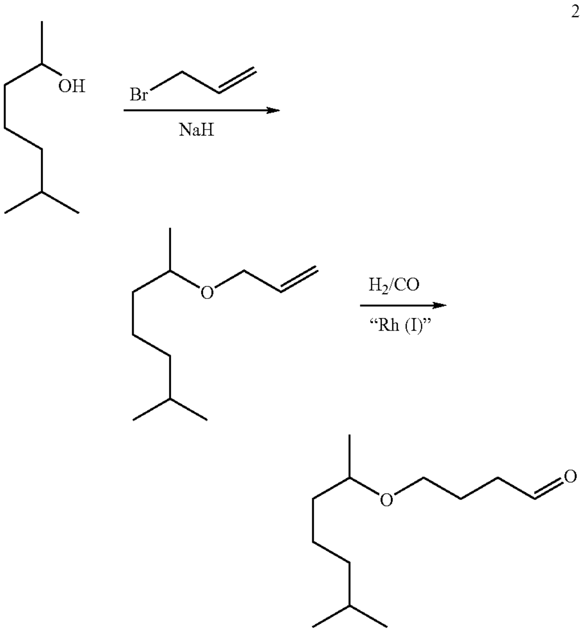

-continued

3

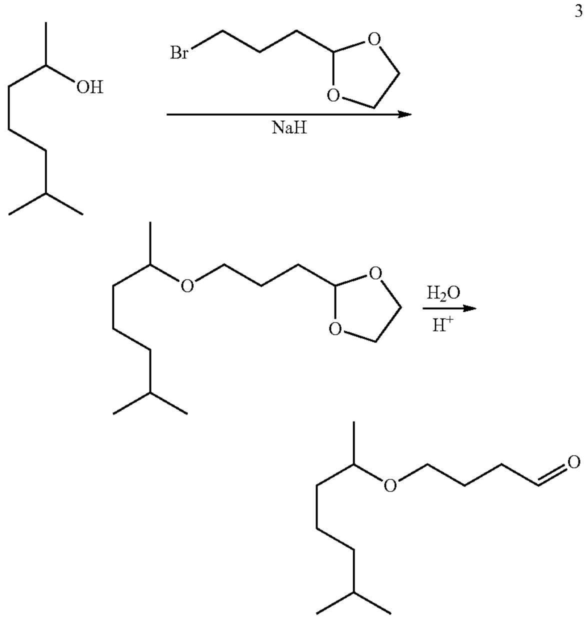

The synthesis of 4-[(1,1,5-trialkylhexyl)oxy]butanals cannot utilise route 1 shown in Scheme 1 but an additional method is available as shown in Scheme 2.

Scheme 2

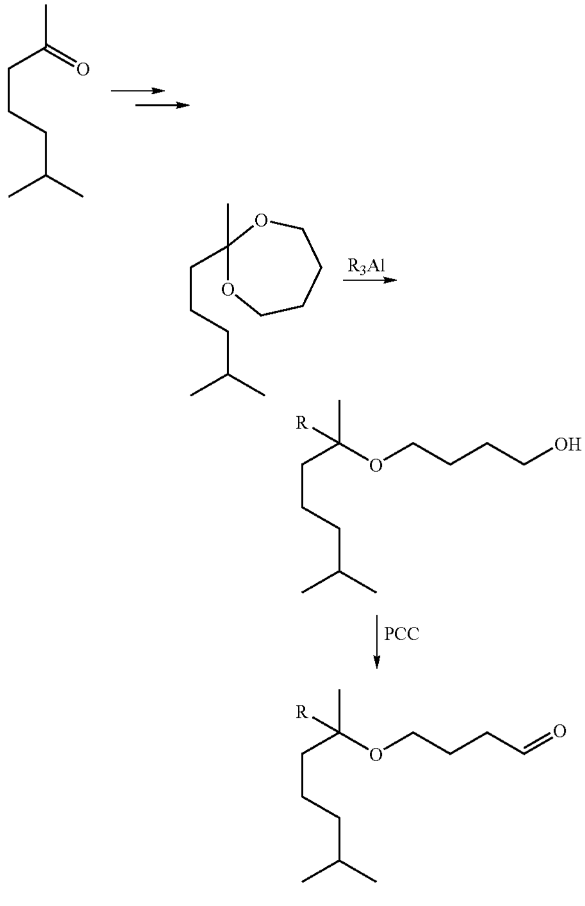

Similarly, the synthesis of enantiomerically pure 4-[(1,5-methylhexyl)oxy]butanal cannot utilise the acetal route depicted in Scheme 1, thus these materials can be synthesised via route 2 shown in Scheme 1 using the enantiomerically pure 6-methylheptan-2-ol.

The iso-compounds can be obtained via routes such as those shown in Scheme 3.

Scheme 3

1

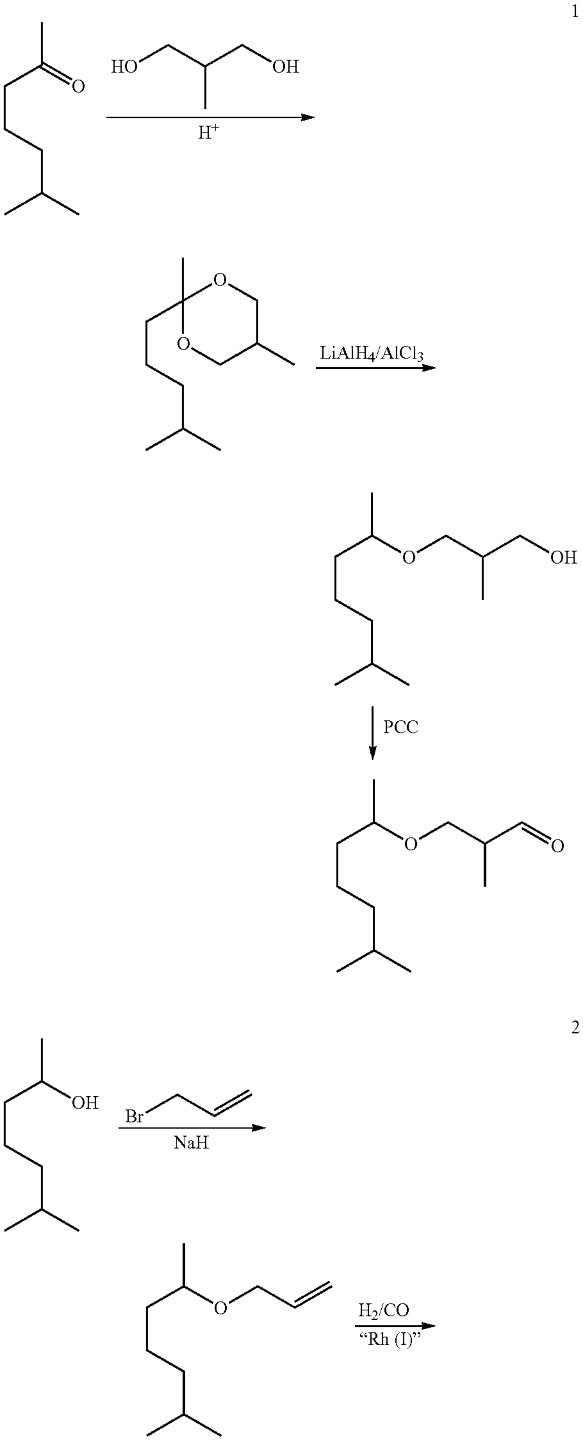

2

-continued

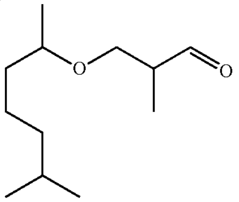

Alternatively, for the 3-[(1,1-dialkylhexyl)oxy]2-methylpropanals, a route similar to that shown in Scheme 2 may be employed (Scheme 4).

Scheme 4

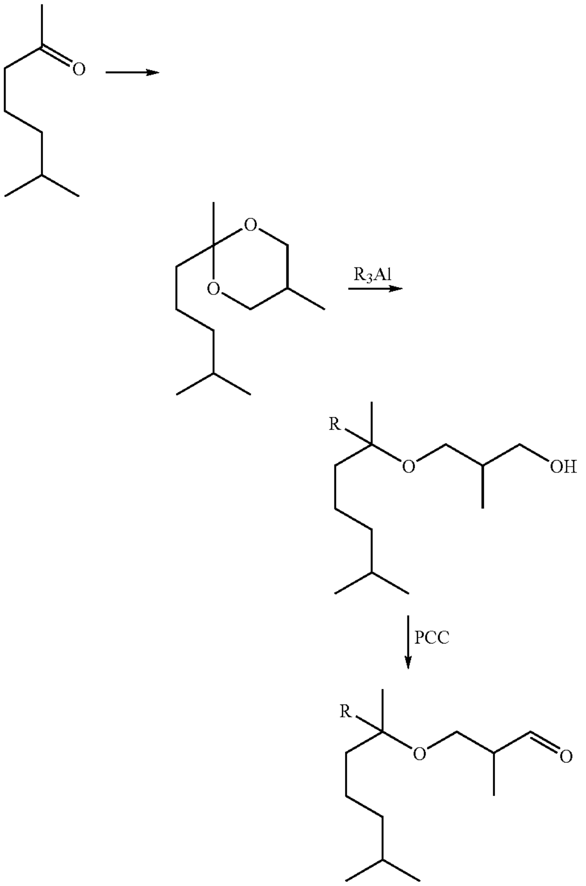

Other Fragrance Materials

Other fragrance materials which can be advantageously combined with one or more fragrance compounds according to the invention in a perfume are, for example, natural products such as extracts, essential oils, absolutes, resinoids, resins, concretes etc., but also synthetic materials such as hydrocarbons, alcohols, aldehydes, ketones, ethers, acids, esters, acetals, ketals, nitriles, etc., including saturated and unsaturated compounds, aliphatic, carbocyclic, and heterocyclic compounds.

Such fragrance materials are mentioned, for example, in S. Arctander, Perfume and Flavor Chemicals (Montclair, N.J., 1969), in S. Arctander, Perfume and Flavor Materials of Natural Origin (Elizabeth, N.J., 1960), "Flavor and Fragrance Materials—1991"\ Allured Publishing Co. Wheaton, Ill. USA and in H Surburg and J Panten, "Common Fragrance and Flavor Materials", Wiley-VCH, Weinheim, 2006 ISBN-13: 978-3-527-31315-0, ISBN-10: 3-527-31315-X.

Examples of fragrance materials which can be used in combination with one or more fragrance compounds according to the invention are: geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenyl-ethanol, 2phenylethyl acetate, benzyl alcohol, benzyl acetate, benzyl salicylate, styrallyl acetate, benzyl benzoate, amyl salicylate, dimethylbenzyl-carbinyl acetate, trichloro-methylphenyl-carbinyl acetate, p-tert-butylcyclohexyl acetate, isononyl acetate, vetiveryl acetate, vetiverol, αhexylcinnamaldehyde, 2-methyl-3-(p-tert-butylphenyl) propanal, 2-methyl-3-(p-isopropylphenyl)propanal, 2-(p-tert-butylphenyl)-propanal, 2,4-dimethyl-cyclohex-3-enyl-carboxaldehyde, tricyclodecenyl acetate, tricyclodecenyl propionate, 4-(4-hydroxy-4-methylpentyl)-3-cyclohexenecarboxyaldehyde, 4-(4-methyl-3-pentenyl)-3-cyclohexenecarboxaldehyde, 4-acetoxy-3-pentyltetrahydropyran, 3-carboxy methyl-2-pentylcyclopentanone, 2-n-heptylcyclopentanone, 3-methyl-2-pentyl-2-cyclopentenone, n-decanal, n-dodecanal, 9-decenol-1, phenoxyethyl isobutyrate, phenylacetaldehyde dimethylacetal, phenylacetaldehyde diethyl acetal, geranyl nitrile, citronellyl nitrile, cedryl acetate, 3-isocamphylcyclohexanol, cedryl methyl ether, isolongifolanone, aubepine nitrile, anisic aldehyde, heliotropin, coumarin, eugenol, vanillin, diphenyl oxide, hydroxycitronellal, ionones, methylionones, isomethylionones, irones, cis-3-hexenol and esters thereof, indane musks, tetralin musks, isochroman musks, macrocyclic ketones, macrocyclic lactone musks, ethylene brassylate.

Solvents which can be used for perfumes which contain a fragrance compound according to the invention are, for example: ethanol, isopropanol, diethyleneglycol mono ethyl ether, dipropylene glycol, diethyl phthalate, triethyl citrate, isopropyl myristate, etc.

The invention will be further described, by way of illustration in the following examples.

EXAMPLE 1

Synthesis of 4-[(5-methylhexyl)oxy]butanal/2-methyl-3-[(5-methylhexyl)oxy]propanal A 3-[(5-methylhexyl)oxy]prop-1-ene Sodium hydride (60% dispersion in mineral oil, 0.8 g, 18 mmol) was charged into a 50 mL reaction flask. Dimethylformamide (10 mL) was added under nitrogen. The 5-methyl-1-hexanol (97% pure, 2.0 g, 17 mmol) in dimethyl formamide (10 mL) was added dropwise at room temperature. The resulting mixture was then stirred at ambient temperature until no more gas was generated (1 h). Allyl bromide (97% pure, 2.3 g, 18 mmol) was added dropwise at ambient temperature over 5 min. The resulting mixture was stirred at ambient temperature for 1 h. GC analysis indicated complete conversion. The reaction mixture was hydrolysed with ice-water (15 mL), extracted with methyltert-butyl ether (3×10 mL) and the combined organic phase was washed with saturated brine, dilute HCl solution and saturated brine. The organic phase was dried over magnesium sulphate and the solvent removed by evaporation. The residue was Kugelrohr-distilled to give the desired product as a colourless oil (95% pure by GC rpa, 2.3 g, 15 mmol, 88% chemical yield).

$^{13}C$ NMR (101 MHz, CHLOROFORM-d) δ ppm 22.57 (q, 2C) 23.97 (t) 27.93 (d) 30.01 (t) 38.82 (t) 70.50 (t) 71.77 (t) 116.61 (t) 135.10 (d)

$^{1}H$ NMR (400 MHz, CHLOROFORM-d) δ ppm 0.85 (d, 6H) 1.17 (m, 2H) 1.28-1.60 (m, 5H) 3.41 (t, 2H) 3.95 (td, 2H) 5.15 (m, 2H) 5.89 (m, 1H)

m/z (relative intensity) 156 ($M^+$, <1), 127 (2), 98 (6), 96 (6), 83 (7), 71 (14), 69 (15), 57 (100), 43 (46), 41 (68).

B 4-[(5-methylhexyl)oxy]butanal/2-methyl-3-[(5-methylhexyl)oxy]propanal

Acetylacetanatodicarbonyl rhodium (I) (0.005 g, 0.02 mmol) and (9,9-dimethyl-9H-xanthene-4,5-diyl)bis(diphenylphosphine) (0.030 g, 0.05 mmol) were added to a 25 mL glass-lined autoclave and dissolved in toluene (3 mL). 1-(allyloxy)-5-methylhexane (2.0 g, 12.2 mmol) was added to the reactor and, following purging with nitrogen, the reaction mixture was subjected to hydroformylation conditions using a 1:1 molar ratio of hydrogen and carbon monoxide gas (30 bar, 60° C., 4 h) with vigorous stirring. The reaction mixture was directly chromatographed on silica gel (hexane/diethyl ether). The isolated products were Kugelrolhr distilled to give 4-[(5-methylhexyl)oxy]butanal (1.4 g, 7.5 mmol, chemical yield 62%) and 2-methyl-3[(5-methylhexyl)oxy]propanal (0.14 g, 6.2%).

Odour (4-[(5-methylhexyl)oxy]butanal): Aldehydic, Fatty, caramel

Odour (2-methyl-3-[(5-methylhexyl)oxy]propanal): Aldehydic, Citrus, Lemon, Nerol Like (4-[(5-methylhexyl)oxy]butanal)

$^{13}C$ NMR (101 MHz, CHLOROFORM-d) δ ppm 22.54 (q, 2C) 22.57 (t) 23.89 (t) 27.89 (d) 29.88 (t) 38.74 (t) 40.93 (t) 69.51 (t) 71.02 (t) 202.31 (d)

$^{1}H$ NMR (400 MHz, CHLOROFORM-d) δ ppm 0.83 (d, 6H) 1.10-1.92 (m, 9H) 2.49 (td, 2H) 3.33-3.42 (2t, 4H) 9.75 (t, 1H)

m/z (relative intensity): (no $M^+$), 142 (3), 127 (4), 114 (2), 96 (77), 83 (14), 71 (60), 57 (100), 43 (57), 41 (39).

(2-methyl-3-[(5-methylhexyl)oxy]propanal)

$^{13}C$ NMR (101 MHz, CHLOROFORM-d) δ ppm 10.68 (q) 22.56 (q, 2C) 23.82 (t) 27.90 (d) 29.73 (t) 38.72 (t) 46.81 (d) 70.77 (t) 71.53 (t) 204.16 (d)

$^{1}H$ NMR (400 MHz, CHLOROFORM-d) δ ppm 0.85 (d, 6H) 1.10 (d, 3H) 1.12-1.56 (m, 7H) 2.61 (q, 1H) 3.36-3.65 (m, 4H) 9.71 (d, 1H)

m/z (relative intensity) 186 ($M^+$, 1), 117 (4), 99 (11), 97 (15), 88 (5), 83 (11), 70 (46), 57 (100), 55 (50), 43 (58), 41 (75).

EXAMPLE 2

Synthesis of 4-[(1,5-dimethylhexyl)oxy]butanal

A 2-methyl-2-(4-methylpent-3-enyl)-4,7-dihydro-1,3-dioxepine

A 2 L 3-necked baffled reaction flask was equipped with a thermocouple pocket, mechanical stirrer and Dean & Stark (D&S) apparatus. 6-methylhept-5-en-2-one (99%+, 1.43 mol, 180 g) was combined with: (2Z)-but-2-ene-1,4-diol (96%, 505 g, 5.5 mol), ammonium chloride (99%+, 4.93 g, 0.09 mol), hydroquinone (1.58 g, 0.014 mol) and cyclohexane (400 mL) in the reaction flask. The reaction contents were heated to reflux using an isomantle and the water formed in the reaction was removed in the D&S trap. Once the reaction had stopped, as observed by GC, the solution was cooled and sodium carbonate added (5% aqueous solution, 500 mL). The reaction was stirred for 5 mins and the solution was transferred to a separating funnel. The phases were allowed to separate and the lower aqueous phase removed. A further water wash (500 mL) ensured that no ammonium chloride remained in the organic phase. The aqueous phases were combined and extracted with cyclohexane (400 mL). The organic phase were combined and washed with water (400 mL) and then dried over magnesium sulphate. Once the solvent had been removed the product was fractionally distilled using a Vigreux column.

The distillation yielded 160.7 g of 2-methyl-2-(4-methylpent-3-enyl)-4,7-dihydro-1,3-dioxepine.

Odour: Floral, citrus, bergamot $^{13}C$ NMR (101 MHz, CHLOROFORM-d) δ ppm 17.59 (q) 21.11 (q) 23.13 (t) 25.63 (q) 36.35 (t) 61.13 (t, 2C) 103.42 (s) 123.91 (d) 129.55 (d, 2C) 131.70 (s)

$^{1}H$ NMR (400 MHz, CHLOROFORM-d) δ ppm 1.36 (s, 3H) 1.60 (s, 3H) 1.66 (s, 3H) 1.73 (m, 2H) 2.02 (m, 2H) 4.23 (s, 4H) 5.10 (t, 1H) 5.64 (t, 2H)

m/z (relative intensity): (no $M^+$), 153 (1), 125 (10), 109 (9), 107 (15), 93 (5), 83 (4), 69 (16), 55 (11), 43 (100).

B 2-methyl-2-(4-methylpentyl)-1,3-dioxepane 2-methyl-2-(4-methylpent-3-enyl)-4,7-dihydro-1,3-dioxepine (98%, 159.6 g, 0.8 mol) was stirred at room temperature with 5% Palladium on Carbon (0.32 g, 0.2% wt/wt) and methanol (132 mL) under hydrogen (0.1-0.5 bar). The pressure was varied to hold a temperature below 30° C. After 2 hrs the exotherm stopped indicating the end of the reaction. Analysis showed that the intermediate 2-methyl-2-(4-methylpent-3-enyl)-1,3-dioxepane had been obtained. A sample was isolated pure and its odour determined as citrus, mandarin, linalool and floral.

$^{13}C$ NMR (101 MHz, CHLOROFORM-d) δ ppm 17.52 (q) 22.30 (q) 23.07 (t) 25.59 (q) 29.71 (2t) 37.59 (t) 61.86 (2t) 102.40 (s) 124.13 (d) 131.43 (s)

$^{1}H$ NMR (400 MHz, CHLOROFORM-d) δ ppm 1.24 (s, 3H) 1.58 (s, 3H) 1.53-1.62 (m, 6H) 1.65 (s, 3H) 1.98 (m, 2H) 3.63 (m, 4H) 5.08 (m, 1H)

m/z (relative intensity): 198 ($M^+$, 3), 126 (11), 115 (28), 111 (23), 108 (42), 93 (16), 83 (13), 71 (33), 69 (33), 55 (70), 43 (100), 41 (56).

More catalyst was added (0.48 g, 0.3% wt/wt) and the pressure increased to 4 Bar and after 11 hrs no further hydrogen was consumed. GC analysis at this time showed that the product contained mainly the desired 2-methyl-2-(4-methylpentyl)-1,3-dioxepane.

The catalyst was filtered from the product and the solvent removed in vacuo. 159.2 g of a coloured oil were obtained which was subsequently distilled (62° C./1-2 mbar). 140 g of purified product was obtained (>99%, 86% chemical yield).

Odour: Floral, fruity, citrus, linalol $^{13}C$ NMR (101 MHz, CHLOROFORM-d) δ ppm 22.19 (t) 22.38 (q) 22.57 (q, 2C) 27.90 (d) 29.75 (t, 2C) 37.90 (t) 39.18 (t) 61.88 (t, 2C) 102.69 (s)

$^{1}H$ NMR (400 MHz, CHLOROFORM-d) δ ppm 0.85 (d, 6H) 1.16 (m, 2H) 1.25 (s, 3H) 1.27-1.59 (m, 9H) 3.64 (m, 4H)

m/z (relative intensity) (no M), 185 (1), 155 (1), 128 (1), 127 (1), 115 (100), 110 (7), 95 (11), 85 (15), 71 (25), 58 (42), 55 (44), 43 (88).

C 4-[(1,5-dimethylhexyl)oxy]butan-1-ol

A 2 L 3-necked reaction flask was equipped with an addition funnel (500 mL), thermocouple pocket, mechanical stirrer and condenser. A slow flow of dry nitrogen was used throughout the reaction. Tetrahydrofuran (750 mL) was charged to the flask and chilled below 10° C. using an ice bath. Aluminium chloride (184.9 g, 1.39 mol) was added over 40 mins ensuring the temperature did not exceed 10° C. Lithium Aluminium Hydride was added over 40 mins again ensuring the temperature did not exceed 10° C. The suspension was stirred for 30 mins. 2-methyl-2-(4-methylpentyl)-1,3-dioxepane (>99%, 138.5 g, 0.69 mol) was diluted in tetrahydrofuran (150 mL) and added to the suspension over 60 mins, again ensuring the temperature remained below 10° C. The reaction was stirred for 2 hrs.

Water (200 g) was added over 90 mins to quench the reaction. This is an extremely exothermic reaction. The product was extracted with two portions of cyclohexane (500 mL) and washed with water (200 mL). The organic phases were combined, dried over magnesium sulphate and the solvent removed under vacuum. Following this procedure 135.9 g of a colourless oil were obtained. This material was distilled using a Vigreux column to give 106.6 g of 4-[(1,5-dimethylhexyl)oxy]butan-1-ol (86% chemical yield).

Odour: Weak, aldehydic, floral, citrus, fatty $^{13}$C NMR (101 MHz, CHLOROFORM-d) δ ppm 19.48 (q) 22.54 (q) 22.58 (q) 23.21 (t) 27.39 (t) 27.87 (d) 30.52 (t) 36.66 (t) 38.98 (t) 62.69 (t) 68.29 (t) 75.78 (d)

$^{1}$H NMR (400 MHz, CHLOROFORM-d) δ ppm 0.84 (d, 6H) 1.11-1.70 (m, 11H) 1.12 (d, 3H) 2.83 (m, 1H) 3.37 (m, 2H) 3.49 (m, 1H) 3.61 (m, 2H)

m/z (relative intensity): (no $M^+$), 129 (1), 117 (4), 112 (2), 97 (3), 89 (6), 73 (100), 71 (23), 55 (53), 43 (31), 41 (25).

D 4-[(1,5-dimethylhexyl)oxy]butanal

A 250 mL 3-necked flask was equipped with a thermocouple pocket, magnetic stirrer and condenser. PCC (13.9 g, 0.64 mols), sodium acetate (1.22 g, 0.015 mol), stavox (0.01 g) and dichloromethane (100 mL) were added to the flask. 4-[(1,5-dimethylhexyl)oxy]butan-1-ol (10.0 g, 0.05 mol) was added over 5 minutes with stirring. The reaction was stirred for 3 hrs at room temperature. After this time the reaction mixture contained ca. 82% of the desired product (RPA GC).

The crude reaction mixture, a dark brown oil (9.3 g), was purified by bulb-to-bulb distillation followed by fractional distillation to give 4-[(1,5-dimethylhexyl)oxy]butanal as a colourless oil (1.8 g, 9 mmol, 18% chemical yield).

Odour: Aldehydic, green, floral, watery, very intensive and diffusive $^{13}$C NMR (101 MHz, CHLOROFORM-d) δ ppm 19.54 (q) 22.54 (q) 22.57 (q) 22.97 (t) 23.25 (t) 27.90 (d) 36.78 (t) 38.99 (t) 41.06 (t) 67.03 (t) 75.56 (d) 202.43 (d)

$^{1}$H NMR (400 MHz, CHLOROFORM-d) δ ppm 0.84 (d, 6H) 1.07 (d, 3H) 1.10-1.5 (m, 7H) 1.83-1.90 (m, 2H) 2.50 (m, 2H) 3.28-3.52 (m, 3H) 9.75 (t, 1H)

m/z (relative intensity): (no $M^+$), 115 (3), 112 (5), 110 (7), 97 (2), 87 (4), 71 (100), 57 (10), 55 (7), 43 (24), 41 (14).

EXAMPLE 3

Synthesis of 4-{[(1S)-1,5-dimethylhexyl]oxy}butanal/3-{[(1S)-1,5-dimethylhexyl]oxy}-2-methylpropanal A (2S)-6-methylheptan-2-ol 5% Palladium on carbon (0.02 g), (2S)-6-methylhept-5-en-2-ol (4.0 g, 3 mmol) and methanol (20 mL) were added to a 50 mL round-bottomed flask fitted with a magnetic stirrer. The flask was evacuated and then pressurised with 1 bar of hydrogen from a balloon. This was repeated three times then the reaction mixture was stirred for 8 hours at room temperature under hydrogen. The crude reaction mixture was filtered and the solvent removed in vacuo to yield (2S)-6-methylheptan-2-ol (3.4 g, 26 mmol, chemical yield 85%), suitable for the next stage.

Odour: Fruity, pine-American $^{13}$C NMR (101 MHz, CHLOROFORM-d) δ ppm 22.55 (q, 2C) 23.46 (q) 23.52 (t) 27.91 (d) 38.92 (t) 39.58 (t) 68.15 (d)

$^{1}$H NMR (400 MHz, CHLOROFORM-d) δ ppm 0.85 (d, 6H) 1.17 (d, 3H) 1.12-1.20 (m, 2H) 1.20-1.44 (m, 4H) 1.46 (s, 1H) 1.52 (h, 1H) 3.77 (m, 1H)

m/z (relative intensity): (no $M^+$), 115 (4), 112 (2), 97 (15), 84 (11), 69 (22), 55 (34), 45 (100), 43 (29).

B 3-{[(1S)-1,5-dimethylhexyl]oxy}prop-1-ene

Sodium hydride (60% dispersion in mineral oil, 2.9 g, 72 mmol) and dimethylformamide (100 mL) were charged to a 250 mL three-necked flask fitted with thermocouple, magnetic stirrer, condenser and dropping funnel. To the reaction mixture was added a solution of (2S)-6-methylheptan-2-ol (3.1 g, 24 mmol) in dimethylformamide (10 mL). This reaction mixture was stirred at room temperature for 1 hr then allyl bromide (8.6 g, 72 mmol) was added dropwise over 10 minutes ensuring the reaction temperature did not rise significantly (41° C. was observed). The reaction mixture was stirred for a further 20 minutes until the reaction was complete. To the reaction mixture was added water (10 mL) and the resultant mixture was extracted with methyltert-butyl ether (2×100 mL). The combined organic phase was dried over magnesium sulphate and the solvent remove in vacuo to yield a yellow oil which was chromatographed over silica gel (hexane/methyltert-butyl ether) to give 3-{[(1S)-1,5-dimethylhexyl]oxy}prop-1-ene as a sl. yellow oil (2.7 g, 15.8 mmol, chemical yield 66%).

Odour: Metallic, vegetable $^{13}$C NMR (101 MHz, CHLOROFORM-d) δ ppm 19.63 (q) 22.58 (q) 22.61 (q) 23.28 (t) 27.94 (d) 36.85 (t) 39.04 (t) 69.33 (t) 74.92 (d) 116.26 (t) 135.63 (d)

1H NMR (400 MHz, CHLOROFORM-d) δ ppm 0.85 (d, 6H) 1.10-1.19 (m, 2H) 1.12 (d, 3H) 1.23-1.58 (m, 5H) 3.42 (m, 1H) 3.91 (m, 2H) 5.19 (m, 2H) 5.91 (m, 1H)

m/z (relative intensity) 170 ($M^+$, <1), 155 (1), 113 (7), 97 (5), 95 (7), 85 (100), 71 (14), 69 (12), 57 (25), 55 (19), 43 (83), 41 (86).

C 4-{[(1S)-1,5-dimethylhexyl]oxy}butanal/3-{[(1S)-1,5-dimethylhexyl]oxy}-2-methylpropanal Acetylacetanatodicarbonyl rhodium (I) (0.0087 g, 0.03 mmol) and (9,9-dimethyl-9H-xanthene-4,5-diyl)bis(diphenylphosphine) (0.042 g, 0.07 mmol) were added to a 50 mL glass-lined autoclave and dissolved in toluene (12 mL). 3-{[(1S)-1,5-dimethylhexyl]oxy}prop-1-ene (2.48 g, 14 mmol) was added to the reactor and, following purging with nitrogen, the reaction mixture was subjected to hydroformylation conditions using a 1:1 molar ratio of hydrogen and carbon monoxide gas (35 bar, 60° C., 9 h) with vigorous stirring. The reaction mixture was evaporated in vacuo to yield a yellow viscous oil which was chromatographed over silica gel (hexane/methyltert-butyl ether). 4-{[(1S)-1,5-dimethylhexyl]oxy}butanal was further purified by Kugelrohr distillation to yield the pure product (420 mg, 2.1 mmol, chemical yield 15%). 3-{[(1S)-1,5-dimethylhexyl]oxy}-2-methylpropanal (100 mg, 0.5 mmol, chemical yield 4%) was also obtained.

Odour (4-{[(1S)-1,5-dimethylhexyl]oxy}butanal): Aldehydic, floral, green, watery, more intensive and diffusive than racemic Odour (3-{[(1S)-1,5-dimethylhexyl]oxy}-2-methylpropanal): Aldehydic, citrus, marine (4-{[(1S)-1,5-dimethylhexyl]oxy}butanal)

$^{13}$C NMR (101 MHz, CHLOROFORM-d) δ ppm 19.54 (q) 22.54 (q) 22.57 (q) 22.97 (t) 23.25 (t) 27.90 (d) 36.78 (t) 38.99 (t) 41.06 (t) 67.03 (t) 75.56 (d) 202.43 (d)

$^{1}$H NMR (400 MHz, CHLOROFORM-d) δ ppm 0.84 (d, 6H) 1.07 (d, 3H) 1.10-1.5 (m, 7H) 1.83-1.90 (m, 2H) 2.50 (m, 2H) 3.28-3.52 (m, 3H) 9.75 (t, 1H)

m/z (relative intensity) (no $M^+$), 115 (3), 112 (5), 110 (7), 97 (2), 87 (4), 71 (100), 57 (10), 55 (7), 43 (24), 41 (14).

Enantiomeric purity determined by chiral gc as greater than 97% (ChiralDEX B-DM, 30 m×0.25 mm (Astec), Constant Flow 2 ml/min, helium carrier, Oven temperature 50° C. to 90° C. @ 3°/min, hold 60 mins, then 90° C. to 200° C. @ 5°/min, retention time 54 minutes)

(3-{[(1S)-1,5-dimethylhexyl]oxy}-2-methylpropanal)

$^{13}$C NMR (101 MHz, CHLOROFORM-d) isomer 1: δ ppm 10.71 (q) 19.46 (q) 22.57 (q, 2C) 23.23 (t) 27.89 (d) 36.74 (t) 38.94 (t) 47.01 (d) 68.57 (t) 76.12 (d) 204.44 (d) isomer 2: 10.77 (q) 19.43 (q) 22.57 (q, 2C) 23.22 (t) 27.89 (d) 36.71 (t) 38.95 (t) 47.00 (d) 68.44 (t) 76.06 (d) 204.38 (d)

$^{1}$H NMR (400 MHz, CHLOROFORM-d) two isomers: δ ppm 0.84 (2d, 12H) 1.08-1.20 (2d & m, 16H) 1.28-1.56 (m, 10H) 2.58 (m, 2H) 3.30-3.72 (m, 6H) 9.71 (2d, 2H)

m/z (relative intensity) (no $M^+$), 129 (4), 115 (64), 97 (17), 87 (13), 84 (8), 71 (76), 57 (42), 55 (48), 45 (97), 43 (86), 41 (100).

EXAMPLE 4

Synthesis of 4-[(1-ethyl-1,5-dimethylhex-4-enyl)oxy]butanal/3-[(1-ethyl-1,5-dimethylhex-4-enyl)oxy]-2-methylpropanal A 6-(allyloxy)-2,6-dimethyloct-2-ene Sodium hydride (60% dispersion in mineral oil, 6.8 g, 170 mmol) and dimethylformamide (100 mL) were added to a three necked 500 mL flask fitted with thermocouple, condenser and addition funnel. To the stirred reaction mixture was added dropwise 3,7-dimethyloct-6-en-3-ol (22 g, 139 mmol) at room temperature. The mixture was stirred for 1 hr, cooled to ice bath temperature then allyl bromide (97% pure by GC RPA, 19 g, 15 mmol) was added dropwise whilst maintaining cooling. After a further 3 hr stirring ice/water was added to the reaction mixture and then extracted with methyltert-butyl ether (3×30 mL). The combined organic phase was washed with dilute hydrochloric acid (100 mL), saturated brine (100 mL) and dried with magnesium sulphate. The solvent was removed in vacuo and the residue fractionally distilled to give 6-(allyloxy)-2,6-dimethyloct-2-ene (25.4 g, 92% pure by GC RPA, 118 mmol, chemical yield 70%).

$^{13}$C NMR (101 MHz, CHLOROFORM-d) δ ppm 7.98 (q) 17.56 (q) 22.21 (t) 22.65 (q) 25.68 (q) 30.43 (t) 37.43 (t) 62.09 (t) 76.83 (s) 115.51 (t) 124.67 (d) 131.22 (s) 136.10 (d)

$^{1}$H NMR (400 MHz, CHLOROFORM-d) δ ppm 0.85 (t, 3H) 1.11 (s, 3H) 1.41-1.54 (m, 4H) 1.60 (s, 3H) 1.67 (s, 3H) 1.96 (dt, 2H) 3.83 (dt, 2H) 5.18 (m 3H) 5.26 (m, 1H)

m/z (relative intensity): 196 ($M^+$, <1), 167 (2), 138 (34), 123 (9), 113 (30), 109 (75), 95 (13), 81 (10), 69 (64), 55 (18), 41 (100).

B 4-[(1-ethyl-1,5-dimethylhex-4-enyl)oxy]butanal/3-[(1-ethyl-1,5-dimethylhex-4-enyl)oxy]-2-methylpropanal Acetylacetanatodicarbonyl rhodium (I) (0.069 g, 0.23 mmol) and (9,9-dimethyl-9H-xanthene-4,5-diyl)bis(diphenylphosphine) (0.171 g, 0.29 mmol) were added to a 50 mL glass-lined autoclave and dissolved in toluene (2 mL). 6-(allyloxy)-2,6-dimethyloct-2-ene (10 g, 58 mmol) was added to the reactor and, following purging with nitrogen, the reaction mixture was subjected to hydroformylation conditions using a 1:1 molar ratio of hydrogen and carbon monoxide gas (25 bar, 50° C., 4 h) with vigorous stirring. The reaction mixture was chromatographed over silica gel (hexane/diethyl ether) to give the individual desired products. These were Kugelrohr distilled to give 4-[(1-ethyl-1,5-dimethylhex-4-enyl)oxy]butanal (5.9 g, 26 mmol, chemical yield 45%) and 3-[(1-ethyl-1,5-dimethylhex-4-enyl)oxy]-2-methylpropanal (3.8 g, 17 mmol, chemical yield 30%).

Odour (4-[(1-ethyl-1,5-dimethylhex-4-enyl)oxy]butanal): Floral, aldehydic, muguet Odour (3-[(1-ethyl-1,5-dimethylhex-4-enyl)oxy]-2-methylpropanal): Floral, watery, muguet, citrus, orange (4-[(1-ethyl-1,5-dimethylhex-4-enyl)oxy]butanal)

$^{13}$C NMR (101 MHz, CHLOROFORM-d) δ ppm 7.88 (q) 17.51 (q) 22.14 (t) 22.44 (q) 23.35 (t) 25.63 (q) 30.24 (t) 37.37 (t) 41.22 (t) 59.32 (t) 76.38 (s) 124.61 (d) 131.14 (s) 202.67 (d)

$^{1}$H NMR (400 MHz, CHLOROFORM-d) δ ppm 0.79 (t, 3H) 1.03 (s, 3H) 1.34-1.48 (m, 4H) 1.57 (s, 3H) 1.64 (s, 3H) 1.80-1.95 (m, 4H) 2.47 (td, 2H) 3.27 (t, 2H) 5.06 (t, 1H) 9.74 (t, 1H)

m/z (relative intensity): (no $M^+$), 138 (36), 123 (11), 109 (75), 95 (20), 81 (11), 71 (100), 69 (81), 55 (19), 41 (75).

(3-[(1-ethyl-1,5-dimethylhex-4-enyl)oxy]-2-methylpropanal)

$^{13}$C NMR (101 MHz, CHLOROFORM-d) δ ppm 7.84 (q) 10.77 (q) 17.52 (q) 22.11 (t) 22.25 (q) 25.64 (q) 30.22 (t) 37.37 (t) 46.99 (d) 61.17 (t) 76.57 (s) 124.55 (d) 131.23 (s) 204.70 (d)

$^{1}$H NMR (400 MHz, CHLOROFORM-d) δ ppm 0.80 (t, 3H) 1.06 (s, 3H) 1.08 (d, 3H) 1.36-1.50 (m, 4H) 1.58 (s, 3H) 1.65 (s, 3H) 1.90 (dt, 2H) 2.53 (dt, 1H) 3.47 (d, 2H) 5.07 (t, 1H) 9.70 (d, 1H)

m/z (relative intensity): (no $M^+$), 197 (1), 143 (4), 138 (40), 123 (14), 109 (100), 95 (16), 81 (12), 73 (42), 69 (95), 55 (26), 41 (81).

EXAMPLE 5

Synthesis of 5-[(1,5-dimethylhexyl)oxy]pentanal

A 2-{4-[(1,5-dimethylhexyl)oxy]butyl}-1,3-dioxolane

Sodium hydride (60% dispersion in mineral oil, 0.83 g, 20 mmol) and dimethylformamide (70 mL) were charged to a 250 mL three necked flask fitted with thermocouple, magnetic stirrer, condenser and dropping funnel. To the reaction mixture was added dropwise over 10 minutes 6-methylheptan-2-ol (2.77 g, 21 mmol). The reaction mixture was stirred at room temperature for 90 minutes then water (10 mL) was added. The reaction mixture was poured into water (100 mL), extracted with methyltert-butyl ether (2×100 mL), the combined organic phase dried over magnesium sulphate and the solvent removed in vacuo. The pale yellow oil was chromatographed over silica gel to yield 2-{4-[(1,5-dimethylhexyl)oxy]butyl}-1,3-dioxolane as a colourless oil (1.4 g, 73% pure by GC RPA, 3.9 mmol, chemical yield 19%).

B 5-[(1,5-dimethylhexyl)oxy]pentanal

{4-[(1,5-dimethylhexyl)oxy]butyl}-1,3-dioxolane (1.4 g, 43% pure by GC RPA, 3.9 mmol), acetic acid (10 mL), tetrahydrofuran (16 mL) and water (20 mL) were added to a 100 mL three-necked flask fitted with thermocouple, magnetic stirrer and condenser. The reaction mixture was refluxed for 2 hrs, cooled and saturated sodium carbonate (150 mL) added. The crude reaction mixture was extracted with hexane (4×100 mL), the combined organic phase dried over magnesium sulphate, filtered and the solvent removed in vacuo. The crude product was chromatographed over silica gel (hexane/methyltert-butyl ether) to yield pure 5-[(1,5-dimethylhexyl)oxy]pentanal as a colourless oil (0.22 g, 1.02 mmol, chemical yield 26%).

Odour: Aldehydic, Marine, Floral $^{13}C$ NMR (101 MHz, CHLOROFORM-d) δ ppm 19.04 (t) 19.65 (q) 22.57 (q) 22.60 (q) 23.32 (t) 27.92 (d) 29.57 (t) 36.87 (t) 39.01 (t) 43.65 (t) 67.71 (t) 75.47 (d) 202.59 (d)

$^{1}H$ NMR (400 MHz, CHLOROFORM-d) δ ppm 0.85 (d, 6H) 1.09 (d, 3H) 1.11-1.75 (m 11H) 2.44 (m, 2H) 3.33 (m, 3H) 9.75 (t, 1H)

m/z (relative intensity): 214 ($M^+$, <1), 129 (6), 112 (1), 101 (4), 85 (100), 67 (12), 57 (20), 43 (19), 41 (19).

EXAMPLE 6

Synthesis of [(1,5-dimethylhexyl)oxy]acetaldehyde

A 2-methyl-2-(4-methylpentyl)-1,3-dioxolane 6-methylheptan-2-one (75 g, 590 mmol), ethylene glycol (72.5 g, 1170 mmol), toluene (200 mL) and para-toluenesulphonic acid monohydrate (1.5 g, 2 wt %) were charged into a 500 mL reaction flask fitted with a thermocouple, magnetic stirrer and Dean & Stark apparatus. The reaction mixture was heated to reflux temperature and the water generated during the reaction was collected in the Dean & Stark trap. Once the rate of water collected ceased (after 14 hrs) the reaction mixture was cooled and transferred to a separating funnel. The reaction mixture was washed with 5 wt % aqueous sodium carbonate (200 g) and water (200 g). The organic phase was dried over magnesium sulphate, filtered and the toluene removed by evaporation. The crude product was fractionally distilled to give the desired product as a colourless oil (100% pure by GC rpa, 72 g, 410 mmol, 71% chemical yield).

Odour: Floral, fruity, aldehydic $^{13}C$ NMR (101 MHz, CHLOROFORM-d) δ ppm 21.90 (t) 22.56 (q, 2C) 23.67 (q) 27.95 (d) 39.14 (t) 39.43 (t) 64.57 (t, 2C) 110.17 (s)

$^{1}H$ NMR (400 MHz, CHLOROFORM-d) δ ppm 0.85 (d, 6H) 1.10-1.20 (m, 2H) 1.30 (s, 3H) 1.31-1.62 (m, 5H) 3.92 (m, 4H)

m/z (relative intensity): (no $M^+$), 157 (12), 95 (4), 87 (100), 69 (6), 55 (3), 43 (28).

B 2-[(1,5-dimethylhexyl)oxy]ethanol

Tetrahydrofuran (600 mL) was charged to 2 L flask fitted with condenser, nitrogen, thermocouple and mechanical stirrer. The flask was cooled to <10° C. and the flask was inerted with dry nitrogen fed a slow rate. Aluminium chloride (112 g, 840 mmol) was slowly added to the reaction flask whilst maintaining a temperature of <10° C. Then lithium aluminium hydride powder (15.9 g, 420 mmol) was added slowly over 30 minutes. The reaction mixture was stirred for a further 30 minutes at <10° C. To the reaction flask was added slowly a solution of 2-methyl-2-(4-methylpentyl)-1,3-dioxolane (72 g, 420 mmol) in tetrahydrofuran (50 mL) over 30 minutes. The reaction mixtures as stirred for 2 hours at <10° C. Ethyl acetate (200 g) was then added slowly to the reaction mixture to neutralise the excess lithium aluminium hydride—cooling was necessary to counteract the large exotherm. The crude reaction mixture was extracted into methyltert-butyl ether (2×300 mL) and the organic phase washed with water (200 mL). The organic phase was dried over magnesium sulphate, filtered and the solvent removed by evaporation to yield the desired product suitable for the next synthetic step as a colourless oil (100% pure by GC rpa, 70 g, 400 mmol, 96% chemical yield). A small sample was Kugelrohr distilled to give material suitable for olfactive analysis.

Odour: Floral, green, fatty $^{13}C$ NMR (101 MHz, CHLOROFORM-d) δ ppm 19.61 (q) 22.55 (q) 22.56 (q) 23.28 (t) 27.89 (d) 36.75 (t) 38.99 (t) 62.08 (t) 69.26 (t) 75.95 (d)

$^{1}H$ NMR (400 MHz, CHLOROFORM-d) δ ppm 0.85 (d, 6H) 1.12 (d, 3H) 1.14-1.57 (m, 7H) 2.20 (t, 1H) 3.35-3.72 (m, 5H)

m/z (relative intensity): (no $M^+$), 159 (1), 113 (5), 97 (9), 89 (100), 71 (18), 69 (12), 57 (22), 55 (19), 45 (63), 43 (22), 41 (17).

C [(1,5-dimethylhexyl)oxy]acetaldehyde

Dichloromethane (25 mL), 2-[(1,5-dimethylhexyl)oxy]ethanol (5 g, 29 mmol), a solution of potassium bromide (0.34 g, 2.9 mmol) in water (4.72 g) and 2,2,6,6-tetramethyl-1-piperidinyloxy (TEMPO, 0.053 g, 0.34 mmol) was charged to 100 mL flask fitted with addition funnel, condenser, nitrogen, thermocouple and mechanical stirrer. A 2.8 wt % aqueous solution of sodium hypochlorite (173.5 g, 65 mmol) was added and the reaction stirred for a total of 15 hrs. The product was extracted with hexane (200 ml) and washed with water (2×200 ml). The organic phase was dried over sodium sulphate, filtered and the solvent removed by evaporation to yield a colourless oil (3.9 g). This oil (2 g) was chromatographed over silica gel (methyltert-butyl ether/hexane) to yield the product as a colourless oil (1.18 g, equating to a total chemical yield of 25%).

Odour: Aldehydic, green, floral, very strong.

$^{13}C$ NMR (101 MHz, CHLOROFORM-d) δ ppm 19.38 (q) 22.55 (q) 22.58 (q) 23.19 (t) 27.91 (d) 36.56 (t) 38.94 (t) 74.10 (t) 77.06 (d) 201.87 (d)

$^{1}H$ NMR (400 MHz, CHLOROFORM-d) δ ppm 0.86 (m, 6H) 1.07-1.20 (m, 5H) 1.24-1.60 (m, 5H) 3.47 (m, 1H) 4.04 (m, 2H) 9.73 (t, 1H)

m/z (relative intensity): (no $M^+$), 143 (13), 129 (7), 113 (50), 97 (7), 87 (23), 71 (92), 69 (23), 57 (100), 55 (36), 43 (68), 41 (40).

EXAMPLE 7

4-[(1,5-dimethylhexyl)oxy]butanal 10% DPG was incorporated into a typical Muguet accord as shown in the table below.

| | |
|---|---|
| CITRONELLA CHINESE PURE | 0.2 |
| LINALOL | 2.5 |
| BENZYL ACETATE EXTRA | 1 |
| CYCLAMEN ALDEHYDE EXTRA ™[1] | 0.8 |
| INDOLENE ™[2] | 2 |
| HEXYL CINNAMIC ALDEHYDE | 16 |
| HYDROXYCITRONELLAL | 54 |
| CORPS 98 ™[3] | 1.5 |
| GERANIOL PURE | 4 |
| PHENYL ETHYL ALCOHOL | 16 |
| 4-[(1,5-dimethylhexyl)oxy]butanal 10% DPG | 2 |

[1]3-(4-isopropylphenyl)-2-methylpropanal: origin Givaudan, Switzerland
[2]8,8-di-1H-indol-1-yl-2,6-dimethyloctan-2-ol: origin Givaudan, Switzerland
[3](2-benzyl-1,3-dioxolan-4-yl)methanol: origin Symrise, Germany The rendition was spectacular and brought thickness and intensity which is very welcome in this kind of olfactive area.

EXAMPLE 8

Performance in Candle Wax

Candle wax house base (IGI hard paraffin wax mix) was dosed at 1.0%—candles were left to mature at room temperature for 24 hours before assessment. All ingredients were used as 10% dilutions in benzyl benzoate. Intensity was assessed, by a panel of perfumers, from candle placed in fragrance booths for one hour. All candles were first evaluated in the cold wax before burning. Candles were then burned for one hour, in the fragrance booth, and odour assessed again for the burn mode intensity.

Cold Wax—Very strong, very good throw from cold wax. Excellent strength. Long lasting.

The invention claimed is:

1. A perfume composition comprising a solvent or solid substrate and the compound 4-[(1,5-dimethylhexyl)oxy]butanal.

2. A perfume composition according to claim 1, wherein the compound is present in an amount of at least 0.01% by weight.

3. A perfumed product comprising the perfume composition according to claim 1 and a product base.

4. A method of providing a perfumed product with a muguet-like fragrance accord, comprising adding to a product base the perfume composition according to claim 1.

5. The compound 4-[(1,5-dimethylhexyl)oxy]butanal.

6. A compound selected from 4-{[(1R)-1,5-dimethylhexyl]oxy}butanal, 4-{[(1S)-1,5-dimethylhexyl]oxy}butanal, and a racemic mixture thereof.

7. A perfumed product comprising the compound according to claim 5 and a product base.

8. A method of providing a perfumed product with a muguet-like fragrance accord, comprising adding to a product base at least one compound according to claim 5.

9. The perfume composition according to claim 1, wherein the compound is present in an amount of from 0.1 to 80% by weight.

* * * * *